(12) United States Patent
Rosiello

(10) Patent No.: US 7,618,154 B2
(45) Date of Patent: Nov. 17, 2009

(54) COMPACT RECONFIGURABLE ILLUMINATION DEVICE

(76) Inventor: Keith M. Rosiello, 32 Deerfield Rd., Shrewsbury, MA (US) 01545

( * ) Notice: Subject to any disclaimer, the term of this patent is extended or adjusted under 35 U.S.C. 154(b) by 0 days.

(21) Appl. No.: 11/704,022

(22) Filed: Feb. 7, 2007

(65) Prior Publication Data

US 2007/0195521 A1   Aug. 23, 2007

Related U.S. Application Data

(60) Provisional application No. 60/765,932, filed on Feb. 7, 2006.

(51) Int. Cl.
*F21L 4/04* (2006.01)

(52) U.S. Cl. .................. 362/202; 362/203; 362/204; 362/208

(58) Field of Classification Search .......... 362/202, 362/203, 204, 208
See application file for complete search history.

(56) References Cited

U.S. PATENT DOCUMENTS

| | | | |
|---|---|---|---|
| 5,161,879 A | 11/1992 | McDermott | |
| 5,171,086 A * | 12/1992 | Baloochi | 362/188 |
| 6,168,288 B1 | 1/2001 | St. Claire | |
| 6,183,105 B1 | 2/2001 | Parker | |
| 6,386,730 B1 | 5/2002 | Matthews | |
| 6,485,160 B1 | 11/2002 | Sommers et al. | |
| 6,702,452 B2 * | 3/2004 | Jigamian et al. | 362/205 |
| 6,709,129 B2 | 3/2004 | Galli | |
| 7,008,084 B2 * | 3/2006 | Galli | 362/373 |
| 7,083,300 B2 | 8/2006 | Sharrah et al. | |
| 7,140,748 B2 | 11/2006 | Chien | |
| 7,152,993 B2 | 12/2006 | Chan et al. | |
| 7,152,995 B2 * | 12/2006 | Chapman | 362/206 |
| 2005/0007777 A1 * | 1/2005 | Klipstein et al. | 362/244 |
| 2006/0018121 A1 | 1/2006 | Packard et al. | |

* cited by examiner

*Primary Examiner*—Sandra L O'Shea
*Assistant Examiner*—Mark Tsidulko
(74) *Attorney, Agent, or Firm*—Foley & Lardner LLP; Michel Morency; Ralph Trementozzi

(57) ABSTRACT

Methods and apparatus providing a compact illumination device with interchangeable adaptable insert components and a light source heat sink feature are disclosed. A compact illumination device generates high quality illumination with interchangeable insert components enabling the illumination device to functioning independently or in conjunction with existing devices. The heat sink feature includes a heat sink module adaptable to single or multiple LED configurations to provide optimal light quality for differing applications. The heat sink feature provides optimal heat dissipation from the light source and circuitry to maximize functional life of both the components. The illumination device has multiple operational modes that are customizable for application-specific requirements and controlled through mechanisms fully integrated into the housing assembly. The interchangeability of adaptable insert components configurations within the housing assembly reduces manufacturing burden and overall cost to produce each illumination device.

20 Claims, 7 Drawing Sheets

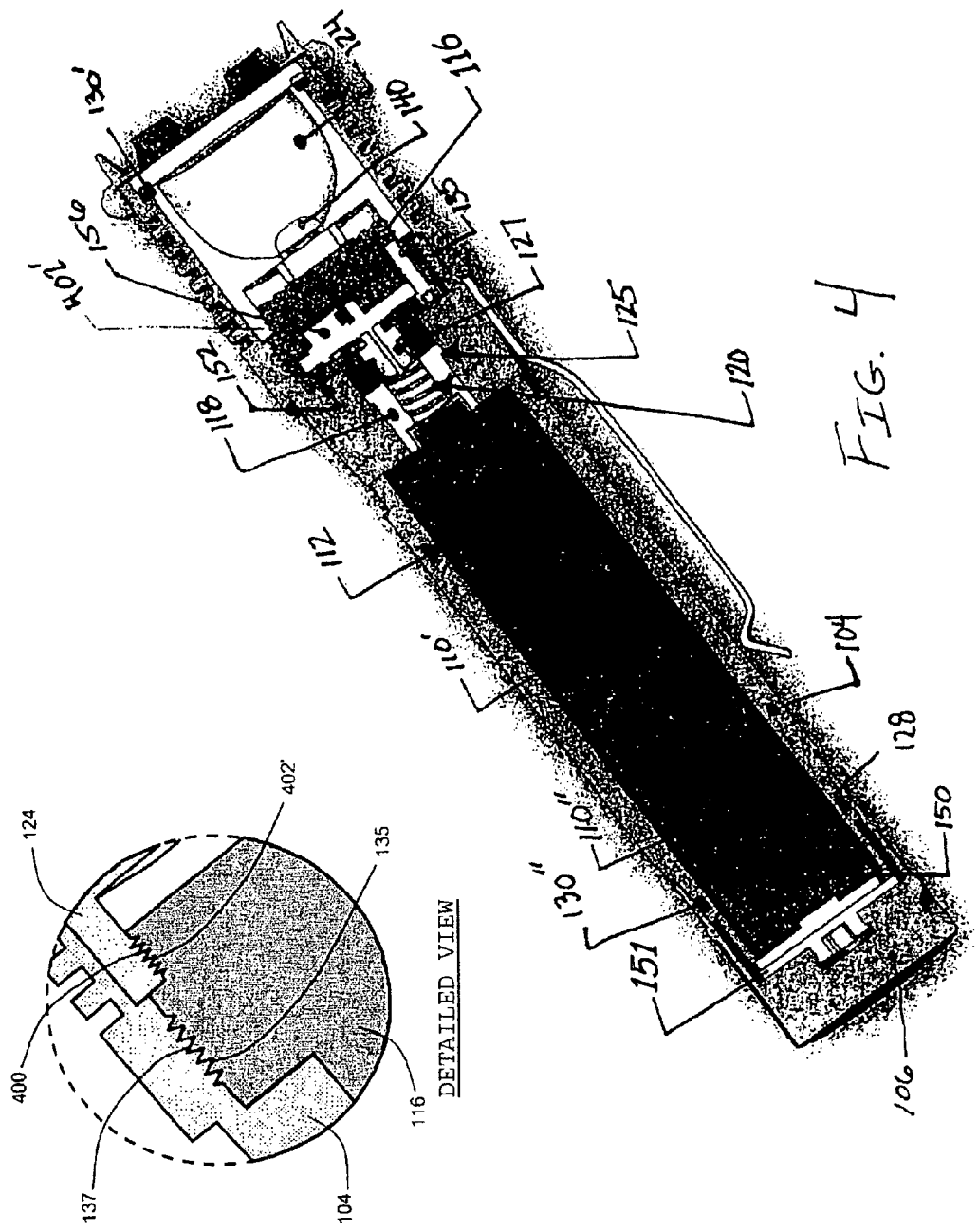

COMPACT RECONFIGURABLE ILLUMINATION DEVICE

CROSS-REFERENCE TO RELATED PATENT APPLICATIONS

The present application claims priority to U.S. Provisional Patent Application No. 60/765,932 filed Feb. 7, 2006, which application is incorporated herein by reference in its entirety.

FIELD OF THE INVENTION

The present invention relates generally to the field of illumination sources. More particularly, the present invention relates to portable or battery-operated illumination sources that are reconfigurable to support a variety of applications.

BACKGROUND OF THE INVENTION

Flashlights are well-known devices that provide a portable source of illumination. Generally, flashlights are comprised of the following components: a housing, a portable power source, one or more light sources, an activation switch, and optionally control circuitry. The basic modes of operation for the common flashlight are a selectable power on state or power off state. Flashlights with unique features or functionality are known in the art. Changes to these devices generally focuses on the particular physical form or characteristic of the housing of the device to, but the functionality remains basic. Other functional innovations with the flashlight include, an integrated rechargeable power source (U.S. Pat. No. 6,183,105), an inline rotational activation switch (U.S. Pat. No. 6,168,288 B1), or a dual-mode operation (U.S. Pat. No. 6,709,129), each incorporated herein by reference in their entireties.

It is becoming more common for some flashlights to include a Light emitting diode (LED) source. LEDs are well-know devices that are compact in size, posses an extremely long functional life, and produce a high quality light output. LEDs are powered through an accompanying circuit board component and are a commonly used light source for flashlights, indicator lights, safety lights, inspection equipment, and remote visualization equipment, such as medical and industrial endoscopes, surgical laparoscopes, locksmith scopes and the like.

SUMMARY OF THE INVENTION

The present invention improves upon other prior functional innovations with the flashlight by providing a highly functional and reliable flashlight that also posses a low manufacturing cost. An interchangeable insert component of the present invention further improves upon the flashlight by enabling the same basic flashlight components to be used in a variety of common and highly specialized applications simply by interchanging interchangeable insert component.

One embodiment of the invention relates to an illumination device including an elongated housing having a proximal end, a distal end, and a cavity therebetween. The cavity is open at the proximal end and configured for receiving a portable power source and a light source assembly configured for positioning within the cavity. The elongated housing also includes a positioning feature securely fastened within the cavity and adapted to retain the light source assembly when positioned therein. The device also includes a retaining ring and an interchangeable light guide configured for positioning within the cavity. The retaining ring is removably fastened to the proximal end of the elongated housing, securely retaining the interchangeable light guide and the light source assembly within the elongated housing when fastened thereto.

Another embodiment of the invention relates to an illumination device including a housing having a battery housing component and a lamp housing component. The battery housing component has threads on one end, further including an inner lumen capable of receiving and containing one or more batteries. The battery housing also has an electrically conductive pathway from the batteries to the lamp housing component. The lamp housing component has a threaded end and a light emitting end, further including one or more open ended lumens, interior features. The lamp housing component includes a gasket adapted to the interior features. The gasket has a base that contacts the inner diameter of the lamp housing component and one or more protrusions having through holes. An outer surface of the protrusions is in contact with an inner surface of the open ended lumens in the lamp housing component. The device also includes one or more light sources positioned through the gasket protrusions and through the open ended lumens; a circuit board in electrical communication with the light sources and the batteries; and a main connector shaft. The shaft is positioned axially through the gasket and circuit board and is capable of securing and holding the lamp housing components. The degree of attachment between the battery housing and the lamp housing through the threaded ends closes or opens the electrical pathway between the light sources and the batteries, wherein the illumination device has interchangeable insert components, LED heat sink module, and housing assembly that can be environmentally sealed.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4 is a cross-sectional view of the components of FIG. 2 shown assembled.

DETAILED DESCRIPTION OF THE PREFERRED EMBODIMENTS

A description of preferred embodiments of the invention follows.

A compact illumination device is provided that generates high quality illumination with interchangeable insert components enabling the illumination device to functioning independently or in conjunction with existing devices. The interchangeable insert components allow a common housing assembly and high quality light source to be employed in a variety of applications, such as flashlight, safety lights, inspection equipment light source, medical and industrial endoscope light source, surgical laparoscope light source, locksmith scope light source and the like. The interchangeability of interchangeable insert components configurations within the housing assembly reduces manufacturing burden and overall cost to produce each illumination device.

Figure 1:
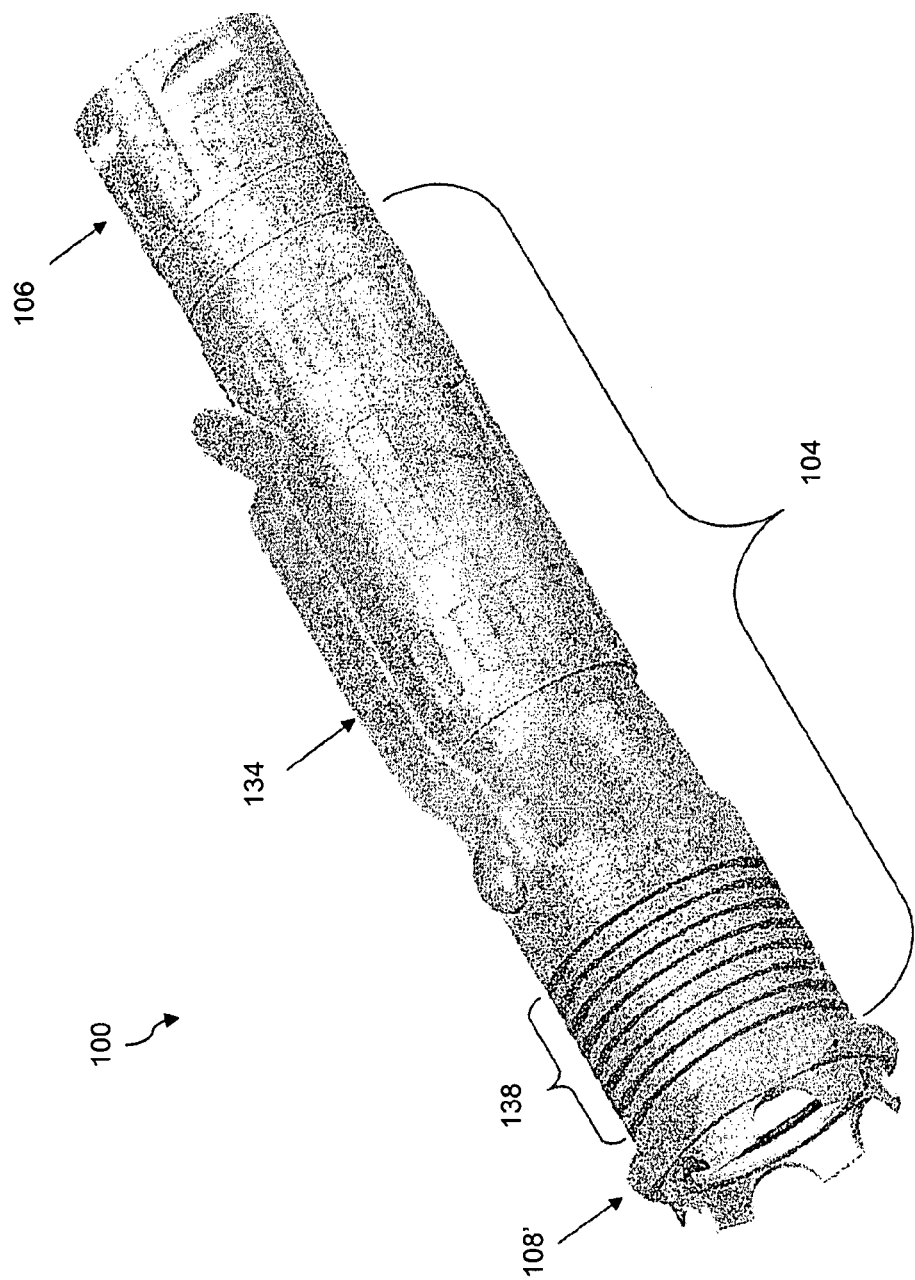
FIG. 1 is a front perspective view of one embodiment of a reconfigurable illumination device according to the principles of the present invention.
Figure 2:
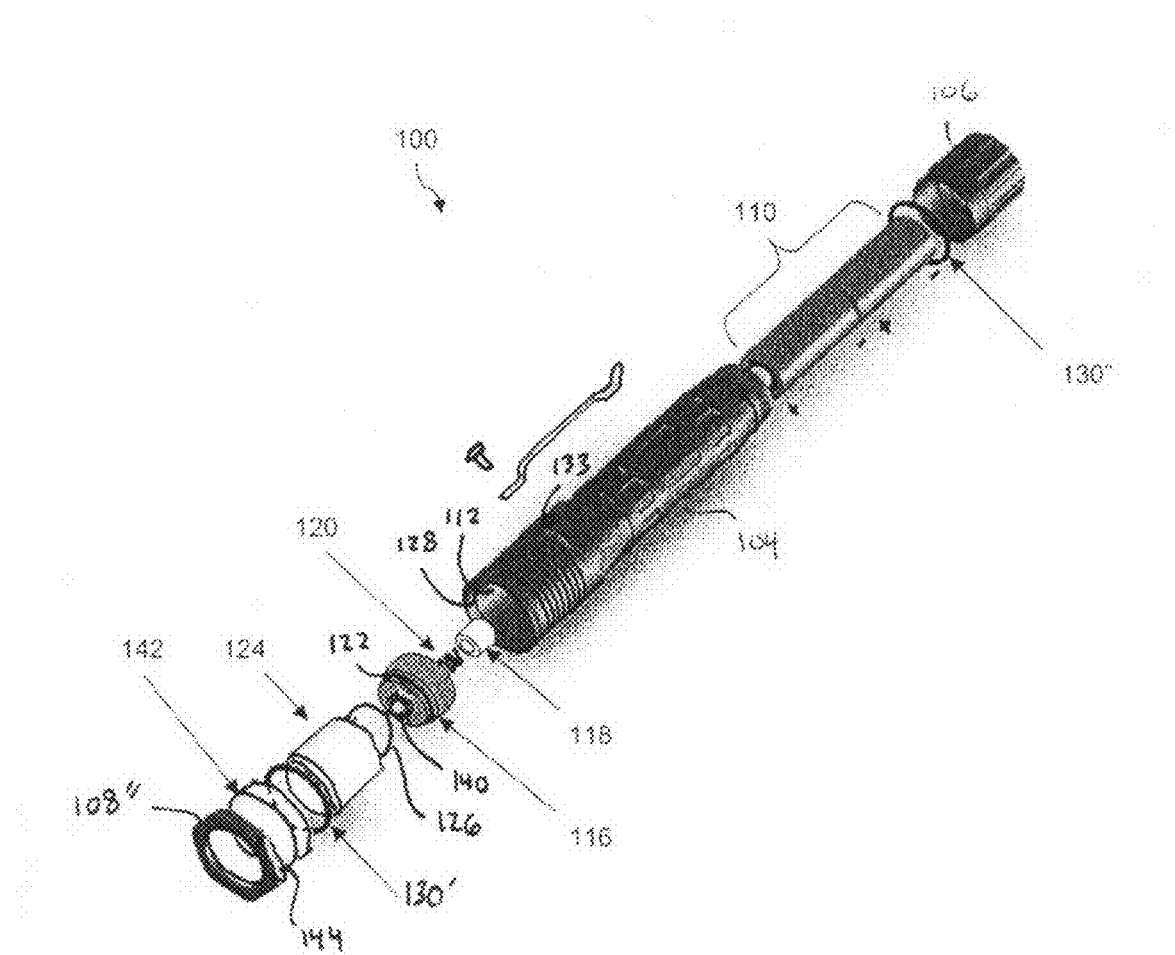
FIG. 2 shows an exploded front perspective view of another embodiment of a reconfigurable illumination device according to the principles of the present invention.

As shown in FIGS. 1 and 2, the preferred embodiment of the disclosed invention is an independent, compact illumination device 100 which takes a substantially cylindrical form. In the preferred embodiment, the device includes a housing assembly 102 comprised of three components: a main housing component 104; an end housing component 106 and an retaining ring component 108', 108" (generally 108). The housing assembly components 104, 106, 108 are assembled together with mating threads. The housing assembly 102 serves to protect internal device components, and in at least some embodiments to function as an actuation and adjustment mechanism.

In an exemplary embodiment, the main housing component 104 features a substantial inner lumen 112 configured for receiving a portable internal power source. The power source can include, for example, two 2016 coin cell lithium 3-volt batteries in series, or one or more AA, AAA, C, or D-cell alkaline batteries or other similar portable power sources. The inner lumen 112 of the main housing component 104 positions the batteries 110', 110" (generally 110) such that their electrical terminals contact one another or an electrically conductive surface at either end of the lumen 112 forming an electrical circuit to provide power to a proximal light source. The main housing component 104 includes an internal alignment feature, such as a first internal shelf 152 (see FIG. 4) to which an LED heat sink module 116 is aligned and anchored. A second shelf 125 provides alignment and mounting for an electrically insulated sleeve component 118. The insulated sleeve component 118 protects a conductive spring component 120, which conducts electrical current from the batteries 110 to circuitry (not shown) on the distal (non-light emitting) side of the LED heat sink module 116 when the device 100 is activated. The sleeve 118 includes a proximal flange that engages the second shelf 125 preventing the sleeve 118 from falling into the power source cavity or even out of the device when the power source is removed or replaced. In some embodiments, a proximal cavity between the first and second shelves 152, 125 allows limited proximal movement. The sleeve 118 and spring 120 provide limited play, ensuring a portable power source contained within the device 100 is allowed some movement while retaining electrical contact.

Alignment features 122 on the proximate (light emitting) side of the LED heat sink module 116 provide for the automatic alignment of an interchangeable insert component 124 with the LED components 116 during the assembly process. In some embodiments, the alignment feature 122 comprises an exterior thread adapted to engage an interior mating thread 402' of the insert component 124' (FIG. 5B). In a preferred embodiment, an environmental seal 126, such as a gasket or curing sealant, is included at the interface of the LED heat sink module 116 and the interchangeable insert component 124 to protect internal components and to increase reliability. Typical limitations of solid state electronic-based illumination devices are a consequence of the inability of these devices to adequately dissipate heat from the circuit board, which results in a truncated service life for the illumination device. The novel heat sink module 116 provides ample thermal conductivity, and consequently extends the service-life of the electrical components. The main housing component 102 also contains alignment features adjacent to the threaded area at each end of the component, such as a groove 128, included specifically to accommodate the placement of environmental seals 130', 130" (generally 130), such as o-rings, to the protect internal components and increase device reliability. In addition, the environmentally sealed housing 102 creates a device that is capable of being sterilized, by any one of the commonly used techniques, such as steam, gamma radiation, or ethylene oxide gas. In some embodiments, the main housing component contains an exterior feature, such as a threaded hole 133, that serves as an attachment point for application specific accessories, such as a clip, clamp, stand or handle. In the preferred embodiment, a clip 134 is mounted to the main housing component using a screw 136 fastened to the threaded hole 133.

In some embodiments, the main housing component 102 contains exterior features 138 to assist in heat dissipation from the LED heat sink module mounted inside. The exterior features 138 can include an array of circumferential comb or fin-like protrusions extending from a exterior surface of the main housing 104. The array of protrusions 138 increase the heat sink's surface area contacting the air, and thus increase the heat dissipation rate. Preferably, the array of protrusions 138 is axially disposed adjacent to the heat sink module 116. At least a circumferential surface of the heat sink module 116 is in thermal communication with an interior surface of the main housing 104. The main housing 104, in turn, is formed from a good thermally conducting material, such as a metal. Thus, heat generated by the light source 140 and electronic assembly 156 (FIG. 4) is conducted by the heat sink module 116. Heat absorbed by the heat sink module 116 is, in turn, conducted to the main housing 104 and dissipated through the array of protrusions 138. In some embodiments, a thermal interface material is used to fill gaps between thermal transfer surfaces to increase thermal transfer efficiency between the heat sink module 116 and the housing 104. A common material for this purpose is a paste or thermal grease, typically including silicone oil filled with aluminum oxide, zinc oxide, or boron nitride.

In the exemplary embodiment, a second housing component, the end housing 106, is assembled to the distal (non-light emitting) end of the main housing component 104 using mating threaded diameters, to facilitate initial assembly as well as battery and environmental seal replacement. In the preferred embodiment, the end housing's primary function is to contain and protect the batteries 110 and is typically constructed from a metal to facilitate this function. In addition, the end housing 106 functions in conjunction with an environmental seal component 130" to protect internal components from environmental hazards and to increase device reliability.

In some embodiments, the end housing 106 also functions as an actuation and adjustment mechanism for the compact illumination device 100. Complementary, mating Class 2 threads can be used on the distal end of the main housing 104 and the end housing 106 to support this functionality. In the preferred embodiment, the electrical connection between the batteries 110 and an LED lamp 140 is comprised of several components that, in combination with the threaded joint between the main and end housings 104, 106, act as an activation switch. The conductive surface 150 and the insulating plate (white component) are individual components. The white insulating plate electrically isolates the conductive surface 150 (hence the batteries) from the end cap component. When the threads connecting the main housing and the end cap component are fully engaged, the distal end of the main housing touches the conductive surface 150, completing the electrical circuit. When the threads are not fully engaged the distal end of the main housing component are not in contact with the conductive surface 150 and therefore break (turn off) the electrical circuit. Since the main housing is part of the electrical circuit, it is manufactured from a conductive metal and then the exterior surfaces are coated with and insulating material.

An insulating plate 151 is provided between the conductive surface 150 and the end housing 106. The insulating plate 151 electrically isolates the conductive surface 150 (hence the batteries) from the end cap component 106. When the threads connecting the main housing 104 and the end cap component 106 are fully engaged, the distal end of the main housing 104 touches the conductive surface 150, completing the electrical circuit. When the threads are not fully engaged the distal end of the main housing component are not in contact with the conductive surface 150 and therefore break (turn off) the electrical circuit. Since the main housing is part of the electrical circuit, it is manufactured from a conductive metal and then the exterior surfaces are coated with and insulating material. Examples of another illumination device incorporating an alternative actuation switch are described in U.S. Patent Application Publication No. US 2006/0018121 A1, published on Jan. 26, 2006 and incorporated by reference herein in its entirety.

In the assembled state all components are aligned co-axially. The electrical circuit is closed by the compressive force generated by the end housing 106 when the threads are maximally engaged with the mating threads in the main housing 104. In the preferred embodiment, this fully engaged position of the end housing 106 on the main housing 104 activates the constant-on operation mode. A slight counter-rotation (e.g., between approximately 2° and 10°) of the end housing 106 back from the constant-on position, engages the momentary activation mode. In this mode of operation, the electrical circuit is open and the light is off, until a nominal proximally directed axial force is applied to an outer surface of the end housing 106, activating the light. When the user-applied force is removed the circuit is opened and the light is off. This mode allows for rapid and sequenced on/off cycling of the light source. The final mode of operation in the preferred embodiment is activated by a significant counter-rotation of the rear housing (approximately 30° or greater), which creates sufficient axial displacement of the electrical contact components for the circuit to remain open independent of any force that is applied to the end housing.

In the preferred embodiment, the retaining ring 108', 108" (generally 108), is assembled to the proximate (light emitting) end of the main housing component 104 using mating threaded diameters. Once assembled to the main housing 104, the retaining ring's primary function is to retain and protect the interchangeable insert components 124', 124", 124''' (generally 124) within the main housing 104. In one embodiment, the interchangeable insert component 124 is configured as a parabolic reflector that directs the light from the LED source 140 to the proximate, open end of the main housing lumen 112. In some embodiments, the retaining ring 108 also retains a transparent protective lens 142 and functions in conjunction with the environmental seal component 130 to protect internal components and increase device reliability. In preferred embodiments, the retaining ring 108 contains exterior features, such as wrench flats 144, to facilitate initial assembly as well as protective lens and environmental seal replacement. The retaining ring 108 may contain additional exterior features specifically designed to provide an application-specific function, such as features to prevent the device 100 from rolling, stand features to hold and aim the device 100, protruding or extending features to protect the device 100 in heavy duty applications, mounting or connection features for use in conjunction with existing devices 100, and features for cosmetic or utilitarian purposes.

Figure 3:
FIG. 3 is a front perspective view of the reconfigurable illumination device of FIG. 2 in an alternate configuration according to the principles of the present invention.

FIG. 3 shows another embodiment of the present invention. This embodiment of the compact illumination device 200 also takes a substantially cylindrical form. A housing assembly 202 is comprised of three components: main housing component 204, end housing component 206, retaining component 208 that are assembled together with mating threads. The housing assembly 202 serves to protect all device components, and function as an actuation and adjustment mechanism. In this embodiment, the main housing component 204 features a substantial inner lumen (not visible) that contains one or more batteries (not visible) and positions them such that the battery electrical terminals contact one another or an electrically conductive surface at either end of the lumen. In this embodiment, the main housing component 204 contains an internal shelf feature (similar to the first internal shelf 152, FIG. 4) to which an LED heat sink module is aligned and anchored. The main housing component 204 also contains exterior, features 210 to assist in heat dissipation from the LED heat sink module mounted inside. In this embodiment, the internal shelf feature of the main housing also provides alignment and mounting for an electrically insulated sleeve component. The insulated sleeve component protects a conductive spring component, which conducts power from the batteries to the circuitry on the distal (non-light emitting) side of the LED heat sink module when the device is activated. Features on the proximate (light emitting) side of the LED heat sink module provide for the automatic alignment of the interchangeable insert component with the LED components during the assembly process. In this embodiment an environmental seal, such as a gasket or applied sealant, is included at the interface of the LED heat sink module and the interchangeable insert component to protect internal components and increase device reliability. In this embodiment, the main housing component 204 also contains features adjacent to the threaded area at each end of the component 204, such as a groove, included specifically to accommodate the placement of environmental seals, such as o-rings, to the protect internal components, increase reliability and provide sterilization capabilities. In this embodiment, the main housing component 204 may contain an exterior feature (not shown), such as a threaded hole, that serves as an attachment point for application specific accessories, such as a clip, clamp, stand or handle.

In this embodiment, the end housing component 206, is assembled to the distal (non-light emitting) end of the main housing component 204 using mating threaded diameters, to facilitate initial assembly as well as battery and environmental seal replacement. In this embodiment, the end housing's primary function is to contain and protect the batteries and is mainly constructed from a metal to facilitate this function. In addition, the end housing 206 functions in conjunction with the environmental seal component to protect internal components and increase device reliability. In this embodiment, the end housing functions as an actuation and adjustment mechanism for the compact illumination device 200. Class 2 threads are used on the distal end of the main housing 204 and the end housing 206 to support this functionality. In this embodiment, the electrical connection between the batteries and the LED lamp is comprised of several components that, in combination with the threaded joint between the main and end housings, act as an activation switch. In the assembled state all components are aligned co-axially. The electrical circuit is closed by the compressive force generated by the end housing when the threads are maximally engaged with the mating threads in the main housing 204. In this embodiment, the fully engaged position of the end housing 206 on the main housing 204 activates the constant-on operation mode.

In this embodiment, the retaining ring component 208 is assembled to the proximate (light emitting) end of the main housing component 204 using mating threaded diameters. Once assembled to the main housing 204, the retaining ring's primary function is to retain and protect an interchangeable insert component 212 within the main housing 204. In this embodiment, interchangeable insert component 212 provides a reliable mechanical connection and optical pathway to an existing remote visualization device, such as a surgical cannula. In this embodiment, the interchangeable insert component is a cylindrical solid containing an axial through-hole 213 with an integral geometric feature, such as a ring component 214 provided to retain a mating end of an external device. In the exemplary embodiment, the through-hole 213 and ring component 214 are designed to accept the cylindrical push-lock style connector, commonly used for the connection of a light source to a device such as a cannula. In this embodiment, the retaining ring 208 contains exterior features, such as wrench flats 216, to facilitate initial assembly as well as protective lens and environmental seal replacement. The retaining ring 208 may contain additional exterior features specifically designed to provide an application-specific function, such as features to prevent the device 200 from rolling, stand features to hold and aim the device, protruding or extending features to protect the device in heavy duty applications, mounting or connection features for use in conjunction with existing devices, and features for cosmetic or utilitarian purposes.

Each configuration of the interchangeable insert component 124 is designed for use with a specific application. In addition to assembling easily with the main housing component, the interchangeable insert component transmits the light from the LED source and, in the case when function with an existing device, provides a means of mechanical connection to that device. The interchangeable insert component allows a generic housing assembly and high quality LED light source to be employed in applications, such as flashlight, safety lights, inspection equipment light source, medical and industrial endoscope light source, surgical laparoscope light source, locksmith scope light source and the like. The interchangeability of interchangeable insert component configurations within the housing assembly reduces manufacturing burden and overall cost to produce each illumination device.

Referring to FIG. 4, a cross-sectional view of the components of FIG. 2 is shown an assembled configuration. The inner lumen 112 of the main housing component 104 is shown with two batteries 110', 110" positioned within. A first terminal (−) of the first battery 110" is in contact with a conductive surface 150 adjacent to an interior end surface of the end housing component 106. A second terminal (+) of the second battery 110' is in contact with a distal end of the conductive spring 120. A second terminal (+) of the first battery 110" is in contact with a first terminal (−) of the second battery 110' resulting in a series connection of the two batteries 110', 110". The main housing component 104 features a substantial inner lumen that contains one or more batteries and positions them such that the battery electrical leads contact one another (in series) or an electrically conductive contact, surface or component of the flashlight. In the preferred embodiment, the interior surface of the battery housing is the electrically conductive surface. The housing is manufactured from an electrically conductive material, such as aluminum, and then the exterior is coated with an insulating material such as aluminum anodize, plastic, ceramic or rubber or other electrical insulating material.

The main housing component 104 includes a second internal shelf feature 125 provided along an interior surface of the inner lumen 112, adjacent to the location of the second terminal (+) of the second battery (110'). In the exemplary embodiment, the second internal shelf feature 125 is an inwardly directed circumferential feature along an interior surface. The second internal shelf feature 125 in cooperation with a complimentary lip of the insulating sleeve 118, prevents the sleeve 118 from moving into the main housing component 104 when batteries are removed.

The main housing component 104 includes a first internal shelf feature 152 provided along an interior surface of the inner lumen 112. In the exemplary embodiment, the first internal shelf feature 152 is an inwardly directed circumferential feature along an interior surface of the inner lumen 112. In some embodiments, the first internal shelf feature 152 does not extend around the entire circumference, but is formed as a series of radially disposed first internal shelf features 152 disposed along the circumference, with gaps therebetween.

Figure 7:
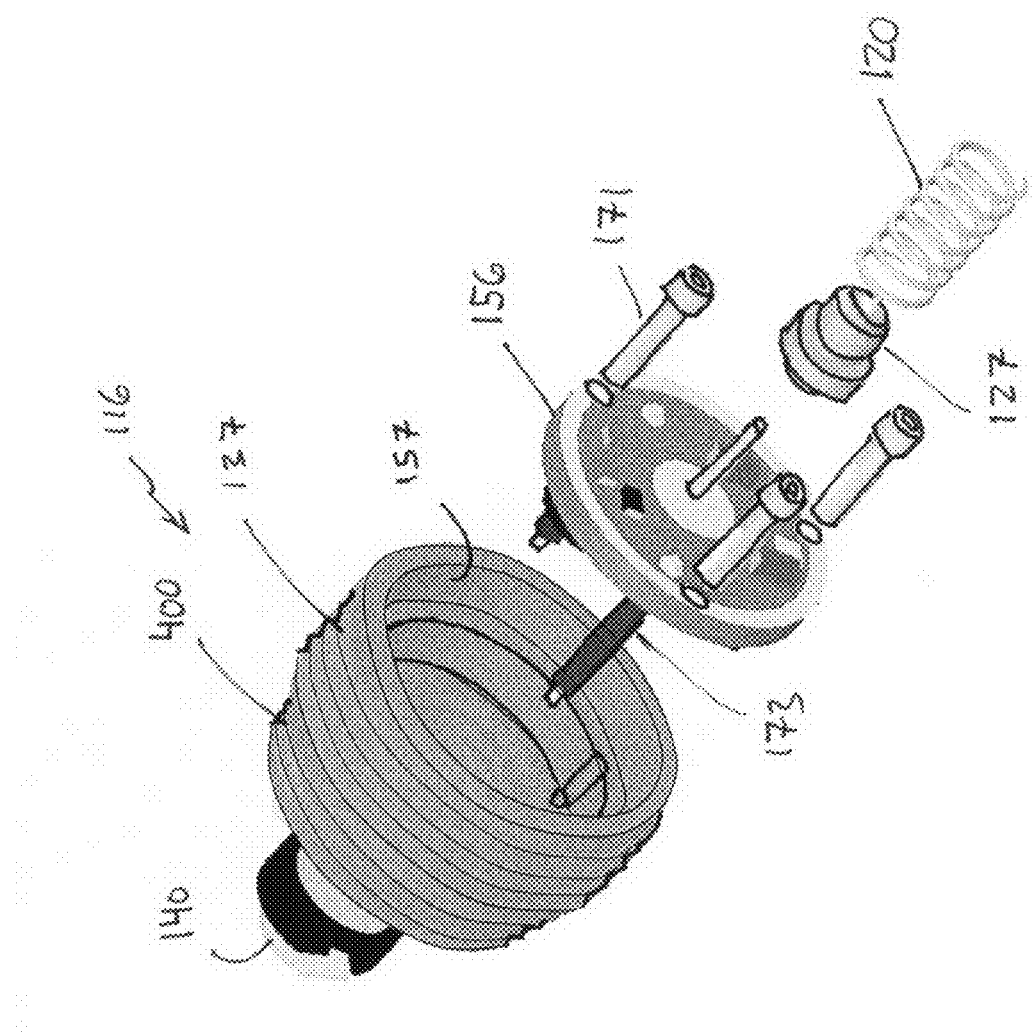
FIG. 7 shows an exploded front perspective view of the light source and heat sink shown in FIG. 2 and FIG. 4.

The main housing component 104 includes an internal thread feature 135, adjacent to the first internal shelf feature 152 on the proximal side. In the exemplary embodiment, the internal thread feature 135 is assembled with a first external thread feature 137 (FIG. 7) on the heat sink module 116. This assembly method facilitates manufacturing and maintains conductivity for a negative terminal of the electrical circuit 156 (FIG. 7). The second external thread feature 400 (FIG. 7) on the heat sink module 116 has a smaller diameter than the primary thread feature and provides for assembly with the internal thread feature 402 on the interchangeable insert component 124. Thus, the multiple threaded features maintain each of the interchangeable insert component 124 and the heat sink module 116 in a fixed axial relationship with respect to the main housing component 104.

The proximal end of the main housing component 104 includes an external thread feature that engages with the internal threads of the retaining ring 108. The retaining ring 108 functions in combination with the environmental seal 130' and the protective lens 142, when provided, to protect internal components and increase device reliability.

The first internal shelf feature 152 is fixedly secured to the main housing component 104. In some embodiments, the first internal shelf feature 152 is integrally formed on the main housing component as can be formed through casting or machining. In other embodiments, the first internal shelf feature 152 can be a separate component inserted and fixedly secured to the interior lumen 112 by any appropriate means, such as mechanical or chemical fasteners, soldering, or welding.

Generally, electronic circuitry 156 is provided between the power source 110 and the illumination source 140 to provide an appropriately conditioned electrical input to the illumination source 140. In the exemplary embodiment using the LED source 140, the electronic circuitry provides a suitable drive current causing the LED 140 to provide optical output of a desired intensity. This circuitry 156 may be as simple as a series-connected resistive element that, in combination with the electric circuit formed by the batteries and the LED, provides a desired bias current. Alternatively or in addition, additional features are provided. For example, protective circuit elements can be included to perform a current limiting function to protect the LED 140 from being over driven. Dimmer circuitry can be provided, such as a pulse width modulator to modulate an LED drive current, whereby a modulation ratio is used to achieve a desired average illumination. Still other circuitry can be provided to select different configuration of a multi-LED embodiment (e.g., illuminate one LED for low beam operation or multiple LEDs for high beam operation). The electronic circuitry 156 can be provided on an electronic circuit board, or as one or more discrete electronic devices disposed adjacent to a distal end of the heat sink module 116. In some embodiments, the electronic circuitry 156 is at least partially housed within a distal cavity formed within the heat sink module.

The illuminating device can be any quality light source such as incandescent bulbs, halogen or xenon bulbs or preferably a solid state light source, such as light emitting diode (LED) lamps with accompanying circuitry. Any of a number of light sources having various wavelength characteristics may be utilized. For example, an infrared, ultraviolet or white light, light sources may be utilized in the flashlight construction. White light is preferred. One or more bulbs can be used. A number of different types of LEDs are available, including air gap LEDs, GaAs light-emitting diodes (which may be doubled and packet as a single unit to offer greater reliability than conventional single-diode packages), polymer LEDs, and semiconductor LEDs. The preferred light source is a conventional single-diode package LED, however the operating wavelength of light source varies, optimized for the end-user application.

The electrically conductive spring 120 is electrically connected between the electronic circuitry 156 and a terminal of one of the batteries 110. In some embodiments, a proximal end of the spring is maintained in a fixed relationship with respect to the electronic circuitry 156. For example, one end of the spring can be fastened to the electronic circuit board 156 using mechanical fasteners, conductive chemical fasteners, solder, a weld or through a combination of these. In the exemplary embodiment, the proximal end of the spring surrounds and maintains electrical contact with a conductive boss component 127, which in turn is mechanically fastened to the electronic circuitry 156. The distal end of the spring 120 is left free floating to selectively contact a terminal at a proximal end of the second battery 110'. The spring 120 is housed within an electrically insulating sleeve 118. The sleeve 118 prevents the spring from inadvertently contacting any portion of the housing 104, which would result in a short circuit when the housing 104 forms part of the electrical circuit coupling the electronic circuitry 156 to a distal end of the first battery 110'.

The internal threads of the end housing 106 are sufficiently engaged with distal end external threads of the main housing component 104, such that the internal conductive surface 150 urges the batteries toward the proximal end of the device 100. Since the heat sink module 116 is in a fixed position, the electrically conductive spring 120 is compressed between the electronic circuitry 156 and the proximal battery terminal. The insulating sleeve 118 is axially displaced toward the proximal end within the interior lumen of the main housing component being urged in a proximal direction by the proximal battery terminal.

When the internal threads of the end housing 106 are sufficiently disengaged from the distal end external threads of the main housing component 104, the distal end of the main housing component is electrically isolated from the conductive surface 150 effectively removing power supply from the light source 140. In some embodiments, the conductive surface 150 and the insulating plate 151 are fixedly attached to the end housing 106, so that the conductive surface axially translates together with the end housing 106.

Each interchangeable insert component 124 configuration is designed for use with a specific application. In addition to assembling easily with the main housing component 104, the interchangeable insert component 124 transmits the light from the LED source 140 and, in the case when function with an external device, provides a means of mechanical connection to that device. Thus, the interchangeable insert component 124 allows a generic housing assembly and high quality LED light source 140 to be employed in applications, such as flashlight, safety lights, inspection equipment light source, medical and industrial endoscope light source, surgical laparoscope light source, locksmith scope light source and the like. The interchangeability of interchangeable insert components 124 configurations within the housing assembly 102 reduces manufacturing burden and overall cost to produce each illumination device.

Figure 5A:
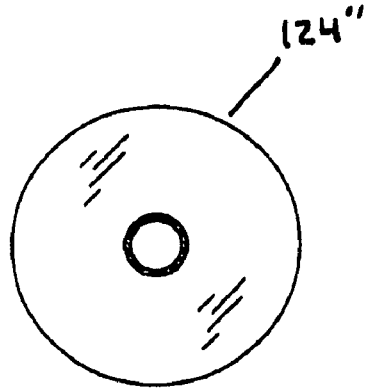
FIG. 5A is a top view of the adaptable insert shown in FIG. 3.
Figure 5B:
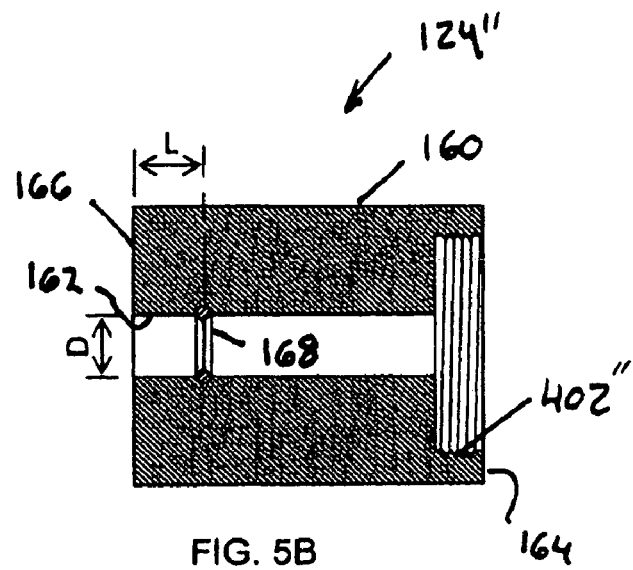
FIG. 5B is a cross-sectional side view of the interchangeable insert shown in FIG. 3.

Referring to FIG. 5A and FIG. 5B, an alternative interchangeable insert component 124' is provided for interconnection to an external device, such as a cannula. The interchangeable insert component 124' includes a cylindrical housing 160 having an external diameter sized to fit within the interior lumen 112 of the main housing component 104. The interchangeable insert component 124' includes an interior thread 402 at its distal end adapted to mate with the proximal thread 400 of the heat sink 116. The threaded engagement securely attaches the insert component 124' to the housing 102 through the heat sink 116.

At least one axial through bore 162 is provided within the cylindrical housing 160 extending from a distal end 164 to a proximal end 166. The shape and diameter of the through bore 162 is determined by the geometry of a mating portion of the external device. For example, the through bore 162 can be cylindrical as shown. In other embodiments, the through bore 162 can have different shapes, such as polygonal, elliptical, or combinations of both. Additionally, a diameter D of the through bore 162 is selected to allow insertion of the mating portion of the external device with a predetermined mechanical tolerance.

In some embodiments, an additional retaining feature is provided within at least a portion of the through bore 162 to retain the mating portion of the external device when inserted into the proximal end 166 of the through bore 162. For example, the through bore 162 includes at lest one circumferential retaining ridge 168 extending partially into the through bore 162 and adapted to retain a corresponding feature of the mating portion of the external device. This ridge can be formed by a compressible ring inserted within a corresponding groove formed within the through bore 162.

Figure 6:
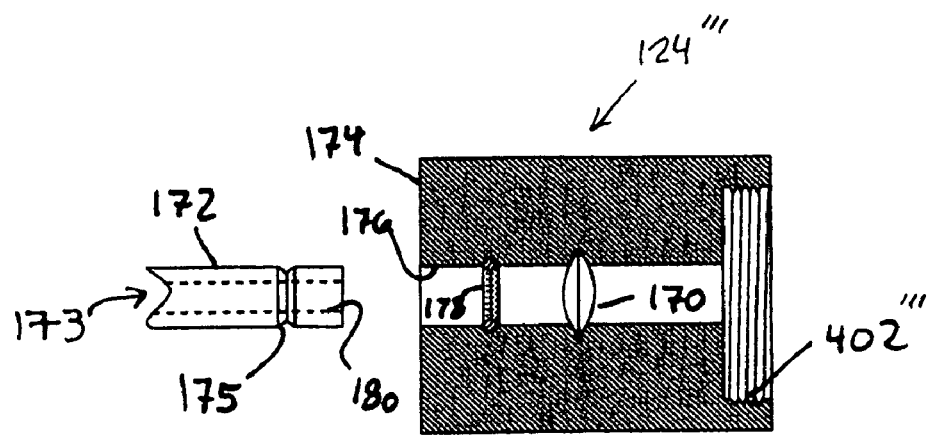
FIG. 6 is a cross-sectional side view an alternative embodiment of an interchangeable insert in alignment with a mating end portion of a light channel.

In other embodiments, additional features can be provided within the interchangeable insert component 124. Referring to FIG. 6, an interchangeable insert component similar to that described above in reference to FIG. 5A and FIG. 5B includes an additional optical element 170. The optical element 170 can be a lens for focusing light emitted from the illuminating source 140 into a mating portion of an external device 173. An exemplary mating portion 172 of an external device 173 is shown in axial alignment with a proximal end 174 of an axial through bore 176. The mating portion 172 includes a circumferential ridge 175 sized and positioned to engage an internal retaining ridge 178 provided within the through bore 176 when inserted therein. The optical element 170 focuses light from the source into an interior light guide 180 of the mating portion 172. In some embodiments, the optical element 170 provides an environmental seal between the external environment and internal components of the device 100 (FIG. 1).

Referring to FIG. 7, an exploded view of an exemplary heat sink module 116 and electronic circuit board assembly 156 is illustrated. The electronic circuit board assembly 156 includes a single axially centered LED 140. The heat sink module 116 includes an axial through bore (not visible) sized and positioned to receive the LED 140, allowing at least a proximal end of the LED 140 to extend therethrough when assembled. The heat sink module 116 can include a first exterior thread feature 400 along a proximal end to facilitate assembly of the interchangeable insert component 124 when the device 100 is assembled. A second exterior thread feature 137 provided along a distal end facilitates assembly of the heat sink module 116 to the main housing 104. In some embodiments, the heat sink module 116 includes a distal cavity 157 configured to house the circuit board assembly 156. The circuit board assembly 156 can be anchored within the distal cavity 157 using one or more fasteners 171.

In an alternative embodiment, the electronic circuit board assembly 156 includes multiple axially directed LEDs 140. A suitable heat sink module includes multiple axial through bores, each sized and positioned to receive a respective one of the LEDs 140, allowing at least a proximal end of each of the LEDs 104 to extend therethrough when assembled. The heat sink module also includes an external thread feature along a proximal end to facilitate assembly of the interchangeable insert component 124 when the device 100 is assembled.

Figure 8:
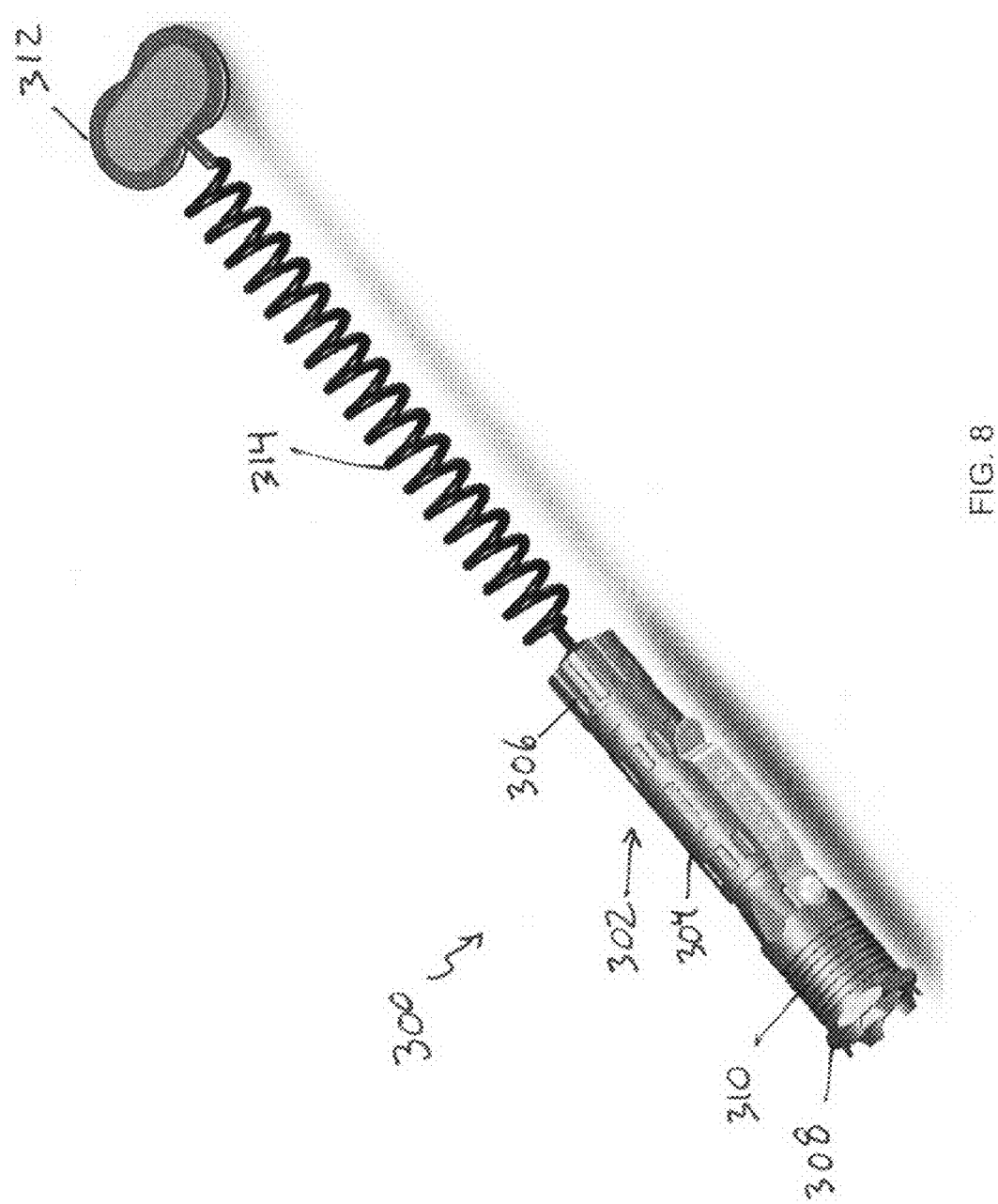
FIG. 8 is a rear perspective view of still another embodiment of a reconfigurable illumination device according to the principles of the present invention.

FIG. 8 shows another embodiment of the present invention. This embodiment of the compact illumination device 300 also takes a substantially cylindrical form. In this embodiment, a housing assembly 302 is comprised of three components 304, 306, 308 that are assembled with mating threads. The housing assembly 302 serves to protect all internal device components. In this embodiment, the main housing component 304 features a substantial inner lumen (not visible) that contains one or more batteries (not visible) and positions them such that the battery electrical terminals contact one another or an electrically conductive surface at either end of the lumen. In this embodiment, the main housing component contains a shelf feature to which an LED heat sink module is aligned and anchored. The main housing component 304 also contains exterior features 310 to assist in heat dissipation from the LED heat sink module mounted inside. In this embodiment, the shelf feature of the main housing also provides alignment and mounting for an electrically insulated sleeve component. The insulated sleeve component protects a conductive spring component, which conducts power from the batteries to circuitry on the distal (non-light emitting) side of the LED heat sink module when the device is activated. Geometric features on the proximate (light emitting) side of the LED heat sink module provide for the automatic alignment of the interchangeable insert component with the LED components during the assembly process. In this embodiment an environmental seal, such as a gasket or applied sealant, is included at the interface of the LED heat sink module and the interchangeable insert component to protect internal components and increase device reliability. In this embodiment, the main housing component 304 also contains geometric features adjacent to the threaded area at each end of the component, such as a groove, included specifically to accommodate the placement of environmental seals, such as o-rings, to the protect internal components, increase reliability and provide sterilization capabilities. In this embodiment, the main housing component 304 may contain an exterior feature (not shown), such as a threaded hole, that serves as an attachment point for application specific accessories, such as a clip, clamp, stand or handle.

In this embodiment, the end housing 306, is assembled to the distal (non-light emitting) end of the main housing component using mating threaded diameters, to facilitate initial assembly as well as battery and environmental seal replacement. In this embodiment, the end housing's primary function is to contain and protect the batteries and is mainly constructed from a metal to facilitate this function. In addition, the end housing functions in conjunction with the environmental seal component to protect internal components and increase device reliability. In this embodiment, the electrical circuit is opened and closed by a remote activation unit 312 that sends a signal using a cable 314, or similar transmission device, which is connected through the end housing 306. A cable passage in the end housing 306 contains an environmental seal component, such as a grommet 316. In this embodiment, the remote activation unit 312 may be one of any commonly known, compact devices such as mounted mechanical button, pressure switch, or the like.

In this embodiment, the retaining ring 308 is assembled to the proximate (light emitting) end of the main housing component using mating threaded diameters. Once assembled to the main housing 304, the retaining ring's primary function is to retain and protect the interchangeable insert component (not visible) within the main housing. In this embodiment, the interchangeable insert component is a reflector that directs the light from the LED source to the proximate, open end of the main housing lumen. In this embodiment, the retaining ring 308 also retains a transparent protective lens and functions in conjunction with the environmental seal component to protect internal components and increase device reliability. In this embodiment the retaining ring contains exterior features, such as wrench flats, to facilitate initial assembly as well as protective lens and environmental seal replacement. The retaining ring may contain additional exterior features specifically designed to provide an application-specific function, such as features to prevent the device from rolling, stand features to hold and aim the device, protruding or extending features to protect the device in heavy duty applications, mounting or connection features for use in conjunction with existing devices, and features for cosmetic or utilitarian purposes.

Ease of manufacture, specifically assembly and electrical connections of the electrical circuit board 156 with the light source 140 and interchangeable insert component 124, is provided by the multiple, interconnecting threaded features 135, 137, 400, 402 on the main housing component 104, heat sink module 116, and interchangeable insert component 124. The electronic subassembly, including the circuit board 156, heat sink module 116 and light source 140 can be assembled independent of the main housing 104, and connected to the main housing 104 by the use of mechanical threads. Mechanical threaded features provide for rapid and proper positioning and secure assembly of the components. Further, the use of mechanical thread features to assemble components facilitates connection of a generic main housing component 104 to multiple configurations of the heat sink module 116. For example, a heat sink module with a single LED, a heat sink module with multiple LEDs, a heat sink module for one or more LEDs with an alternative wavelength or packaged form, or a heat sink module including a fluorescent or incandescent light source. In a similar manner, the assembly of the interchangeable insert component 124 to the heat sink module 116 is facilitated by the use of mechanical threads. For example, providing the ability to connect varying configuration of the interchangeable insert assembly 124 to one or more configurations of the heat sink module 116.

Another novel aspect of this illumination device is the universal low cost to manufacture a high quality illumination devices for a variety of applications. Ease of manufacture enables the provision of multiple configurations of the illumination device for varying applications. The exemplary embodiment can be assembled by first manufacturing the printed circuit board assembly 156 and mounting light source 140 to the circuit board assembly 156 through the electrical leads 173 (FIG. 7). Acceptance and/or functional testing can be performed at this stage on the electrical assembly alone. Manufacture of the device 100 continues by inserting the insulating sleeve 118 into the main assembly 104 through the open proximal end. A proximal flange of the insulating sleeve 118 seats against the second shelf feature 125. The spring 118 is press fit onto the boss 127, which is secured to a distal end of the circuit board assembly 156. The circuit board assembly 156 is secured to a distal end of the heat sink module 116 prior to insertion into the main housing 104. The one or more LEDs 140 are aligned with corresponding bore(s) within a proximal end of the heat sink module 116. The light source assembly including the heat sink module 116, light source 140, and circuit board assembly 156 is then inserted into a proximal end of the main housing 104. The spring 120 is inserted through a bore of the insulating sleeve 118 and the assembly is secured to the main housing 104 using the threaded engagement 135, 137. In some embodiments, such as during initial manufacture, the interchangeable insert component 124 is mounted onto the light source assembly before being inserted into the main housing. In other embodiments, such as during use, the interchangeable insert component 124 is mounted onto the light source assembly after it has been fastened within the main housing 104. A lens and environmental seals can be assembled onto the main housing 104, when provided, and the retaining ring 108 and end housing 106 are attached to the main housing 104 through threaded engagements to complete assembly. Batteries 110 can be inserted through an opening at the distal end by removing the end housing 106.

While this invention has been particularly shown and described with references to preferred embodiments thereof, it should be apparent that unique operational features have been described. Although particular embodiments have been disclosed herein in detail, this has been done by way of example for purposes of illustration only, and is not intended to be limiting with respect to the scope of the appended claims which follow. In particular, it is contemplated by the inventors that various substitutions, alterations, and modifications may be made to the invention without departing from the spirit and scope of the invention encompassed in the appended claims. For instance, the shape and size of the housing, the choice of light spectrum, the addition of electrical control circuitry or the type of power source employed is believed to be matter of routine for a person of ordinary skill in the art with knowledge of the embodiments described herein.

What is claimed is:

1. A reconfigurable illumination device comprising:
    an elongated housing having a proximal end, a distal end, and defining a cavity therebetween, the cavity open at the proximal end and configured to receive a portable power source;
    a light source assembly configured for positioning at least partially within the cavity of the elongated housing;
    an interchangeable light guide also configured for positioning at least partially within the cavity of the elongated housing; and
    a heat sink module in thermal communication with the light source, the heat sink module being secured at one end to an interior surface of the cavity, and removably secured at another end to the interchangeable light guide, the interchangeable light guide being removably coupled to the elongated housing by the heat sink module, the interchangeable light guide also being disposed with respect to the light source assembly to guide at least a portion of light from the light source,
    wherein the interchangeable light guide is removably coupled to the elongated housing by the heat sink module via a first thread on the heat sink module adapted to engage a first mating thread on the interchangeable light guide, and
    wherein the heat sink module is secured to the interior surface of the cavity via a second thread on the interior surface of the cavity adapted to engage a second mating thread on the heat sink module.

2. The reconfigurable illumination device of claim 1, wherein the light source assembly comprises:
    an electronic illumination device; and
    electronic circuit in electrical communication between the electronic illumination device and a portable power source providing a controlled electrical input to the electronic illumination device.

3. The reconfigurable illumination device of claim 2, wherein the electronic illumination device comprises a solid state device.

4. The reconfigurable illumination device of claim 2, wherein the solid state device comprises a light emitting diode (LED).

5. The reconfigurable illumination device of claim 2, wherein the heat sink module comprises an alignment feature configured to engage a distal end of the interchangeable light guide when inserted into the cavity and align the interchangeable light guide with the light source assembly.

6. The reconfigurable illumination device of claim 1, wherein the elongated housing is constructed using a thermally conducting material comprising an external surface feature configured to facilitate heat transfer from the light source assembly.

7. The reconfigurable illumination device of claim 6, wherein the external surface feature comprises an array of fins extending radially outward from the external surface.

8. The reconfigurable illumination device of claim 1, further comprising an internal alignment feature disposed within the cavity for positioning the heat sink module at a fixed axial displaced from the proximal end.

9. The reconfigurable illumination device of claim 8, wherein the internal alignment feature comprises an internal shelf.

10. The reconfigurable illumination device of claim 1, wherein the interchangeable light guide comprises a parabolic reflector.

11. The reconfigurable illumination device of claim 1, further comprising at least one environmental seal positioned to environmentally isolate the cavity.

12. The reconfigurable illumination device of claim 11, wherein the device is sterilized.

13. The reconfigurable illumination device of claim 1 wherein the interchangeable light guide includes a retaining ridge configured for attachment to a mating portion of an external device.

14. The reconfigurable illumination device of claim 1, further comprising an anchor for securing an external accessory to the device.

15. The reconfigurable illumination device of claim 14, wherein the external accessory is selected from the group consisting of: clips, clamps, stands, handles and combinations thereof.

16. The reconfigurable illumination device of claim 1, further comprising an actuator for selectively coupling the light source assembly to a portable power source.

17. The reconfigurable illumination device of claim 16, wherein the actuator includes a threaded end cap removably attached to a distal end of the housing the distal end of the cavity being electrically isolated, wherein actuation is controlled by a degree of threaded attachment of the threaded end cap to the distal end of the housing.

18. The reconfigurable illumination device of claim 16, wherein the actuator is a remote actuator.

19. The reconfigurable illumination device of claim 1, further comprising:
   an electrically conducting spring extending distally from the light source assembly toward a portable power source housed within the cavity; and
   an insulating sleeve defining an axial bore, the electrically conducting spring extending through lithe bore.

20. A reconfigurable illumination device comprising:
   means for storing a portable power source;
   illumination means positioned at least partially within said means for storing said portable power source;
   interchangeable means for guiding light from said illumination means; and
   means for transferring thermal energy away from said illumination means, said means for transferring thermal energy being secured at one end to said means for storing said portable power source, and removably secured at another end to said interchangeable means for guiding light, said interchangeable means for guiding light guide being removably coupled to said means for storing said portable power source,
   wherein said interchangeable means for guiding light is removably coupled to said means for storing said portable power source by said means for transferring thermal energy via a first thread on said means for transferring thermal energy adapted to engage a first mating thread on said interchangeable means for guiding light, and
   wherein said means for transferring thermal energy is secured to said means for storing said portable power source via a second thread on said means for storing said portable power source adapted to engage a second mating thread on said means for transferring thermal energy.

* * * * *